United States Patent
Manna et al.

[11] Patent Number: 5,769,211
[45] Date of Patent: Jun. 23, 1998

[54] MEDICAL HANDPIECE WITH AUTOCLAVABLE SWITCH

[75] Inventors: Ronald R. Manna, Valley Stream; Theodore A. D. Novak, Northport; Scott Isola, Deer Park; David Ng, Brooklyn, all of N.Y.

[73] Assignee: Misonix, Inc., Farmingdale, N.Y.

[21] Appl. No.: 785,989

[22] Filed: Jan. 21, 1997

[51] Int. Cl.⁶ .................................................. H01H 9/06
[52] U.S. Cl. .......................... 200/549; 200/550; 200/505
[58] Field of Search ................................. 200/332.2, 243, 200/505, 522, 530, 534, 537, 547, 549, 550, 60

[56] References Cited

U.S. PATENT DOCUMENTS

| | | |
|---|---|---|
| 2,852,634 | 9/1958 | Garland ....................................... 200/60 |
| 3,995,121 | 11/1976 | Long ......................................... 200/547 |
| 4,057,701 | 11/1977 | Sisk et al. ............................... 200/332.2 |
| 4,492,832 | 1/1985 | Taylor ................................. 200/505 X |
| 5,026,387 | 6/1991 | Thomas . |
| 5,419,761 | 5/1995 | Narayanan et al. . |

*Primary Examiner*—Renee S. Luebke
*Attorney, Agent, or Firm*—R. Neil Sudol; Henry D. Coleman

[57] ABSTRACT

A handle assembly of a medical instrument has a handle with an axis extending from a proximal end of the instrument toward a distal end thereof; and an electrical circuit incorporated at least partially in the handle for controlling an application of an action to a patient via the medical instrument. The circuit has a first electrical contact and a second electrical contact each projecting from a surface of the handle. The electrical contacts are spaced from one another. An actuator ring is slidably disposed on the handle and surrounding the same for motion in alternately opposite directions along the handle under the control of an operator. A bridging electrical contact is disposed on the ring for conductively connecting the first and second electrical contacts at a first predetermined longitudinal position of the ring along the handle, thereby closing the circuit at that position of the ring, and for opening the circuit at another longitudinal position of the ring along the handle. Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

23 Claims, 9 Drawing Sheets

FIG.9B

MEDICAL HANDPIECE WITH AUTOCLAVABLE SWITCH

BACKGROUND OF THE INVENTION

This invention relates to a handpiece for a medical instrument. More particularly, this invention relates to a medical instrument handle with a manually operable switch.

High power ultrasound equipment has found increased application in surgical applications in recent years. Once relegated to open field spinal tumor removal or kidney stone disintegration (lithotripsy), ultrasonic tools have now been successfully used for removing thrombus or plaque in-vivo from arteries or veins, laparoscopic applications such as removal of gall bladders, and soft tissue aspiration of tumors on the liver.

High-power ultrasonic surgical devices generally consist of a generator which produces alternating electrical signals with a frequency above 16 khz and an electromechanical transducer (disposed in a handpiece) of either the piezoelectric or magnetostrictive type which transforms the electrical energy into a mechanical vibration. A probe may also be supplied which amplifies the vibration of the handpiece to a level which will cause cavitation in tissue at a surgical site when the probe tip is brought into contact with the tissue. The cavitation forces ablate or emulsify the targeted tissue, effectively destroying it. In the best systems, the generator contains feedback circuitry to keep the output frequency on or close to the natural resonant frequency of the mechanical system and automatic gain control circuitry which keeps the tip vibrating at a constant amplitude as the load changes.

In practice, the surgeon brings the tip of the vibrating probe near or in contact with unwanted tissue. The ultrasound action is initiated by a remote contact, generally a footswitch or a switch controlled by an operating room nurse. As the tissue is ablated, the resulting emulsion is aspirated by a separate suction cannula or via a bore extending centrally through the handpiece and vibrating tip. U.S. Pat. Nos. 5,026,387 and 5,419,761 describe typical procedures in more detail.

As ultrasound equipment has become increasingly widespread and as surgeons have had more experience with current tooling, several important limitations have come to light. One limitation or inconvenience is the need for a remote switch to initiate the production and emission of ultrasound energy.

For maximum safety, the ultrasound tip cannot remain active continuously. Therefore, the surgeon must be able to turn the unit output on and off as needed. Although a footswitch control is effective for this, the footswitch forces the surgeon, in practice, to balance most of his or her weight on one foot while the other foot is used for the output control. In addition, the surgeon must be able to move around the patient to obtain the best angle of view or manipulation. Moving the footswitch with the surgeon is difficult and sometimes the surgeon looses contact with the pedal, which forces the surgeon to look away from the patient and down to the floor to find the pedal. This activity is distracting and adds to surgeon fatigue and the length of time for the operation.

To alleviate the problems associated with a footswitch control, many surgeons have requested that the handpiece contain a switch for controlling at least the ultrasound output. In some cases, the surgeons have even asked that switches for ancillary equipment such as irrigation and aspiration pumps be placed on the handpiece. Although the concept is intriguing, provision of a manually actuatable switch on the handpiece leads to other problems, both in use and in embodiment.

Generally, when switches have been added to surgical handpieces, the switches have been localized buttons or membrane pads which must be depressed while the unit is in use. This forces the surgeon to keep a thumb or finger on the pad throughout the procedure, which severely limits his ability to rotate or manipulate the handpiece. As rotation of some tooling is necessary for proper clinical efficacy, this restriction on rotation is a major limitation. Increase in fatigue and cramping of the hand have been reported as well. A "push-on/push-off" type control cannot be used, since the surgeon must be able to instantly disengage output when working on delicate areas of the body. When faced with these limitations, most surgeons have opted to return to footswitch control.

Placement of a control switch on the handpiece body is problematic for another reason. Since the handpiece will be in the vicinity of the patient during the operation, the unit must be sterilizable by autoclaving, ETO gas or gamma radiation before reuse. In practice, gamma radiation cannot be specified, as no hospitals or clinics are equipped with this type of sterilizer. ETO gas is also becoming more rare as a clinical sterilant, given that environmental and worker exposure laws are becoming more severe for this chemical. Gas sterilizers also have a very long cycle time, sometimes up to 24 hours. As hospital budgets become more strained, fewer handpieces are available to treat more patients, which requires a very short downtime between procedures. These considerations leave steam autoclaving as the sterilizing method of choice for most facilities. To sterilize instruments by steam autoclave, the articles are cleaned with germicidal soap and water, dried and placed in the autoclave. The instruments are then subjected to high pressure steam at temperatures of 131° C. or greater. The steam causes degradation in dielectric materials, sealants, plastics and metals other than titanium or stainless steels. If steam enters the interior of the handpiece, it will condense to water when cooled and handpiece failure due to shorting of the electrical signal may occur. As the wires for the switch must pass through the housing to the interior, failure of the sealant may allow steam to penetrate. In membrane type switches, the adhesives used have failed, causing delamination failure. Standard type push switches, in addition to the material concerns, are generally not sealed and have failed due to contamination by body fluids which gum the action or coat the contacts.

A need exists, then, for a handpiece that contains a control switch which may be activated by a thumb or any finger placed anywhere in a 360 degree arc, is relatively resistant to contamination by dirt and body fluids, be cleanable and sterilizable, seals the wire connections securely to prevent leakage of steam to the transducer interior and not be degraded by steam autoclaving.

OBJECTS OF THE INVENTION

It is, therefore, an object of the invention to provide a medical handpiece with an improved control switch and, more particularly, a control switch which may be activated by a thumb or any finger placed anywhere in a 360 degree arc.

Another object of the present invention is to provide such a handpiece which is relatively resistant to contamination by dirt and body fluids.

A further object of the present invention is to provide such a handpiece which is cleanable and sterilizable.

Yet another object of the present invention is to provide such a handpiece wherein the wire connections can be securely sealed to prevent leakage of steam to the transducer interior.

These and other object of the present invention will be apparent from the descriptions and drawings herein.

BRIEF DESCRIPTION

A handle assembly of a medical instrument comprises, in accordance with the present invention, a handle having an axis extending from a proximal end of the instrument toward a distal end thereof; and an electrical circuit incorporated at least partially in the handle for controlling an application of an action to a patient via the medical instrument. In the case of a therapeutic or surgical instrument, the action is an operative step affecting selected organic tissues of the patient. The operative step may be the application of microscopic percussive mechanical forces via ultrasonic vibrations, the feeding of irrigation fluid to a surgical site, the suctioning of fluid and particulate material, or the emission of heat energy or electromagnetic radiation. The circuit has a first electrical contact and a second electrical contact each projecting from a surface of the handle. The electrical contacts are spaced from one another. An actuator ring is slidably disposed on the handle and surrounding the same for motion in alternately opposite directions along the handle under the control of an operator. A bridging electrical contact is disposed on the ring for conductively connecting the first and second electrical contacts at a first predetermined longitudinal position of the ring along the handle, thereby closing the circuit at that position of the ring, and for opening the circuit at another longitudinal position of the ring along the handle.

This construction of a medical instrument handle provides a switch on handle which can be actuated easily, e.g., by the operator's thumb, regardless of the angular position of the handle about its longitudinal axis.

The first and second electrical contacts are preferably disposed in a plane oriented transversely to the axis of the handle and are angularly spaced from one another about the axis. More particularly, the surface in which the first and second contacts are located is an annular surface extending in the plane transversely to the axis. The annular surface preferably faces toward the proximal end of the handle, with the first and second electrical contacts projecting from the annular surface toward the proximal end of the handle.

According to a feature of the present invention, a spring is disposed between the handle and the ring for biasing the ring in one direction (toward the proximal end of the instrument) and concomitantly biasing the bridging contact out of engagement with the first and second electrical contacts. The spring thus functions to automatically open the switch upon a relaxation of finger pressure on the actuator ring. There is no need for a second actuation, as where a toggle type actuator switch is provided.

Where the spring is helical, it may be disposed about a pin extending from the annular surface in a proximal direction into a recess provided in the ring. The pin is different from the first and second electrical contacts and serves in part to prevent rotation of the ring relative to the handle. Where the spring is one of two helical springs disposed between the handle and the ring for biasing the bridging contact out of engagement with the first electrical contact and the second electrical contact, the springs are disposed on opposite sides of the handle, with the first and second electrical contacts being disposed at positions displaced 90° from the springs.

In an alternate specific embodiment of the present invention, the spring is a leaf spring attached to the annular surface. In this case, rotation is permitted between the actuator ring and the handle.

In accordance with another feature of the present invention, the actuator ring is provided with an annular flange or cuff extending over the handle and surrounding the contacts so as to define an annular chamber enclosing said contacts. The cuff may be provided along a free edge with an inwardly extending lip, the handle being provided with an outwardly projecting shoulder formation cooperating with the lip to limit axial motion of the ring in one direction, e.g., the proximal direction.

The bridging contact is preferably an annular piece, particularly where the actuator ring is rotatable with respect to the handle. Thus, the switch can be closed irrespective of the relative angular positions of the actuator ring and the handle.

In accordance with a further feature of the present invention, the ring is provided along a radially inner side with a plurality of grooves extending parallel to the axis to define a series of ribs engaging the handle. The grooves and ribs reduce the area of contact between the actuator ring and the handle and concomitantly prevent an accumulation of dirt, grease and sludge which would tend to decrease switch responsiveness.

In another specific embodiment of the handle assembly, the first and second electrical contacts are spring biased. This feature facilitates closure of the switch.

An arrest is advantageously provided on the handle for limiting axial motion of the ring in a proximal direction. This arrest may be the shoulder which cooperates with the inwardly turned lip on the cuff of the actuator ring. Alternatively, another abutment may be provided on the handle proximally of the actuator ring for engaging the ring and preventing proximal motion thereof beyond a pre-established point.

A medical handpiece in accordance with the present invention contains a control switch which may be activated by a thumb or any finger placed anywhere in a 360 degree arc, is relatively resistant to contamination by dirt and body fluids and is cleanable and sterilizable by repeated steam autoclaving. The wire connections are sealed securely to prevent leakage of steam to the transducer interior.

BRIEF DESCRIPTION OF THE DRAWING

In the drawings, like reference numerals are used to designate like parts.

DESCRIPTION OF THE PREFERRED EMBODIMENTS

Figure 1:
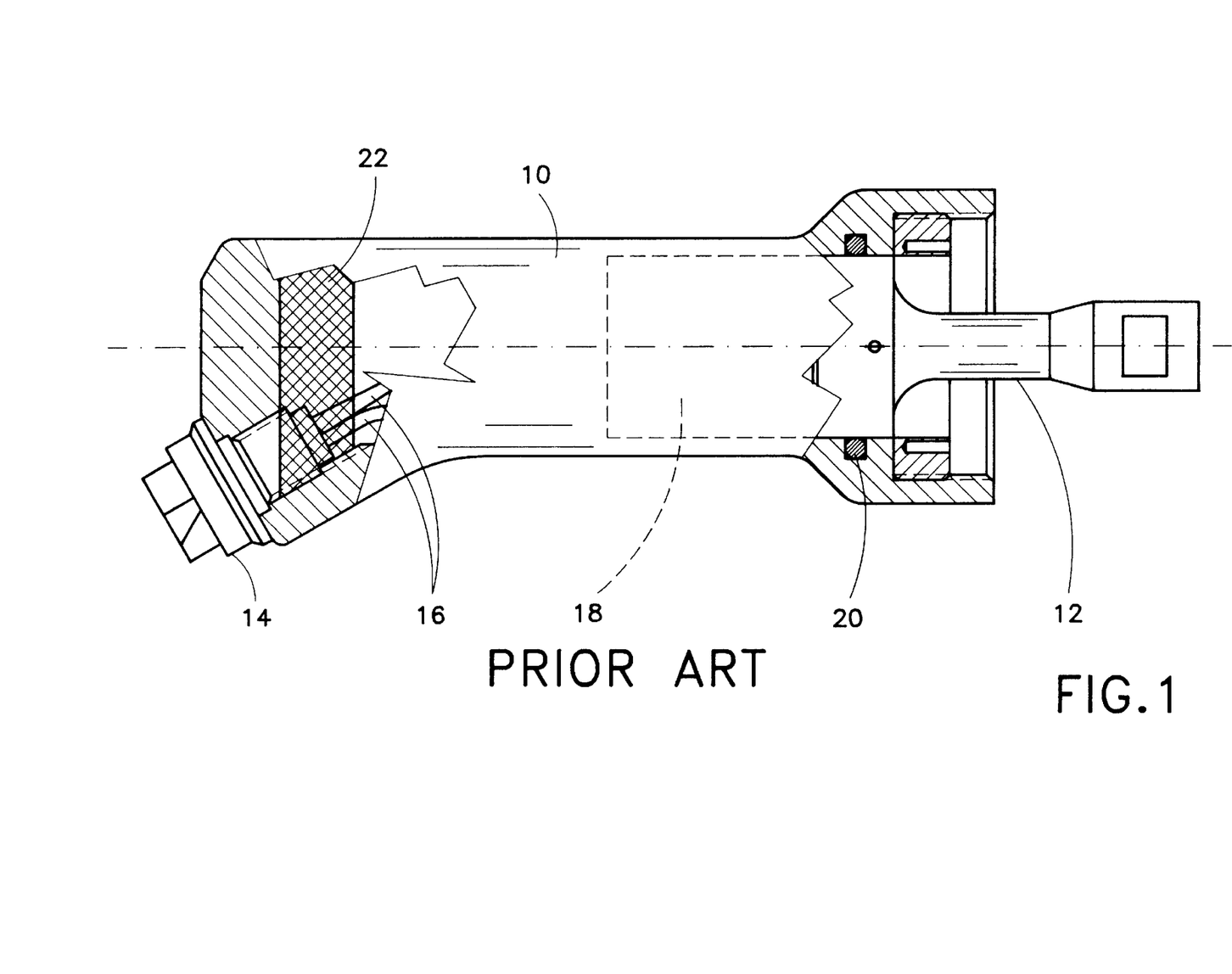
FIG. 1 is a side elevational view, partly in cross-section, of a prior art handpiece for an ultrasonic medical instrument.

FIG. 1 shows a cross section of a typical piezoelectric handpiece of an ultrasonic medical instrument. At one end, a handle body or housing 10 carries an amplification horn 12. At an opposite end is an electrical connector 14. A pair of wires 16 extend from the connector to a piezoelectric crystal assembly 18. Those schooled in the art will realize, however, that the invention described may be applied with equal success to ultrasonic handpieces of the magnetostrictive type, as well as any electromechanical medical handpiece.

The handpiece shown in FIG. 1 allows for sealing against autoclaving by virtue of its one piece housing 10 and O-ring seals 20. All electrical connections are sealed against leakage of steam by using epoxy type sealants applied internally, e.g., at 22. This handpiece has no provisions for controlling the ultrasound power or any other device.

Figure 2A:
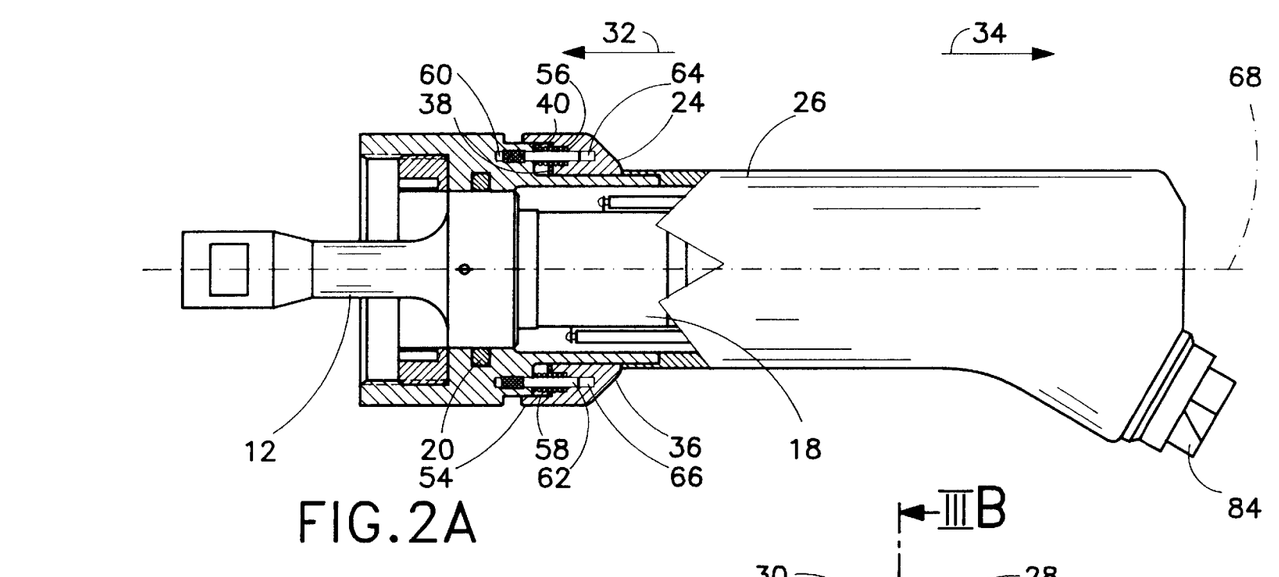
FIG. 2A is a side elevational view, partly in cross-section, of a handpiece for an ultrasonic medical instrument, showing a manually operable switch in accordance with the present invention.
Figure 2B:
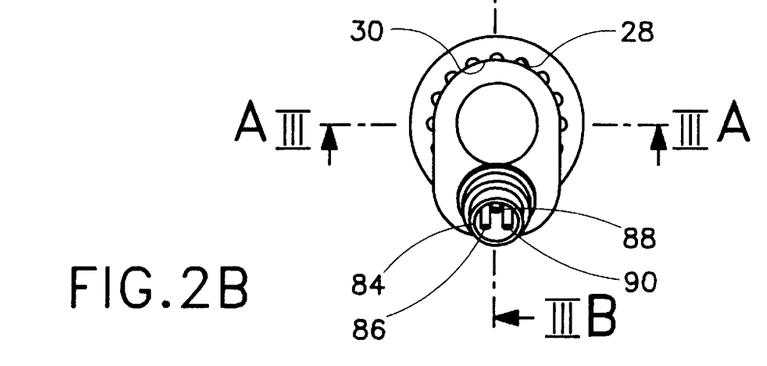
FIG. 2B is a end elevational view of the handpiece of FIG. 2A, taken from a proximal end of the handpiece.

FIGS. 2A and 2B show essentially the same handpiece as FIG. 1 modified to accept an actuator ring 24 which surrounds a substantially cylindrical handle or handpiece case 26. Actuator ring 24 has an internal surface provided with a plurality of angularly equispaced grooves 28 which define a plurality of angularly equispaced ribs 30. Ribs 30 have an internal diameter which is slightly greater than the outside diameter of handpiece case 26 upon which the ribs ride. In this manner, a sliding fit is achieved which allows ring 24 to be translated alternately in a distal direction 32 and a proximal direction 34. A shoulder, ledge or abutment 36 on handpiece case 26 prevents ring 24 from being slid off the back of the unit. Recesses 28 on the inner diameter of ring 24 reduce the amount of material in contact with handpiece case 26. This reduced contact decreases friction and prevents debris from collecting between ring 24 and handpiece case 26, which prevents the ring from sticking or binding.

Ring 24 has a distally directed surface (not designated) which is faced with an electrically conductive lining 38 which does not corrode in the presence of steam or detergents, such as stainless steel. This lining 38 is either glued or staked to ring 24, using methods known to the art. A mating face 40 is fashioned on handpiece case 26. This face is manufactured from a material which is generally nonconductive, such as thermoplastics. Embedded in face 40 are a pair of electrical contacts 42 and 44 (FIG. 3A) in the form of rivets which are electrically conductive and are manufactured from stainless steel. These contact rivets 42 and 44 are attached to wire conductors 46 and 48 which project into the interior of handpiece case 26. Heads 50 and 52 of contact rivets 42 and 44 are not flush with handpiece case face 40, but project some distance from the face. Rivet heads 50 and 52 thus serve as pads which are engaged by the conductive lining 38 of ring 24 when the ring is slid in the distal direction 32. Lining 38 functions as an electrical contact which bridges the distance between rivet heads 50 and 52. Lining 38 is preferably annular, particularly where ring 24 is rotatable about case 26, as discussed below with reference to FIG. 5A.

An annular flange or cuff 54 may be machined or molded onto ring 24 to protect and minimize debris build-up on contact rivets 42 and 44 and lining or bridging contact 38. Cuff 54 extends over casing 26 and defines therewith an annular chamber (not designated) containing contact rivets 42 and 44 and lining or bridging contact 38.

Figure 3A:
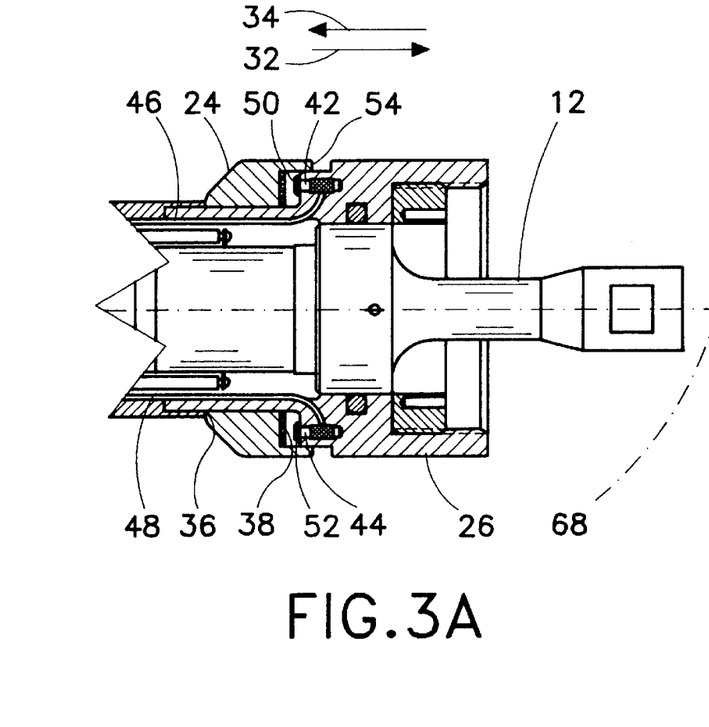
FIG. 3A is a partial longitudinal cross-sectional view taken along line IIIA—IIIA in FIG. 2B.
Figure 3B:
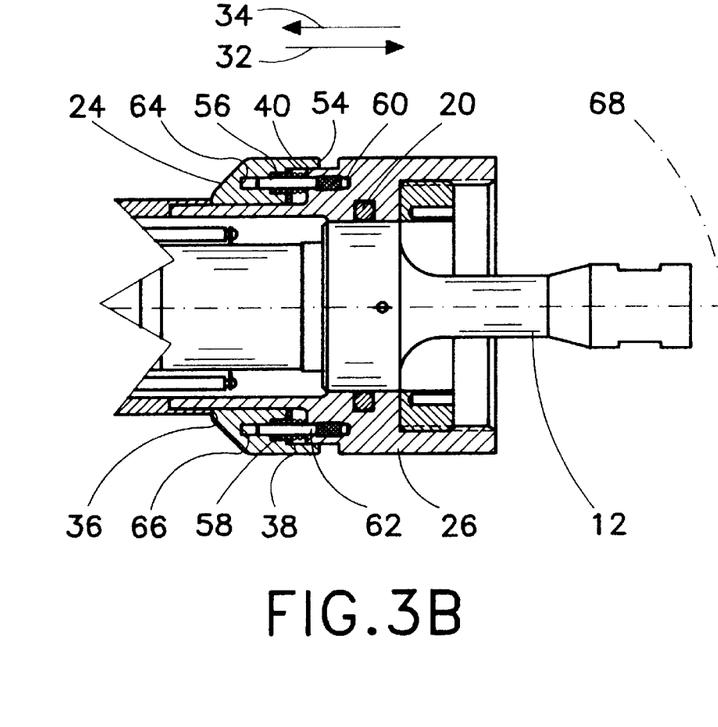
FIG. 3B is a partial longitudinal cross-sectional view taken along line IIIB—IIIB in FIG. 2B.

In order to allow ring 24 to retract automatically, it must be spring loaded. As depicted in FIG. 3B, two helical or coil springs 56 and 58 are placed between ring 24 and handpiece face 40. As shown in FIGS. 3A and 3B together, coil springs 56 and 58 are spaced 90° from each contact rivet 42 and 44. Two pins 60 and 62 are pressed into handpiece face 40 and are thereby fixed in place. Pins 60 and 62 engage blind holes 64 and 66 drilled into ring 24, whereby the pins perform both a locating or mounting function for coil springs 56 and 58 and a keying junction for ring 24 to prevent the ring from rotating about a longitudinal axis 68 of handpiece case 26.

Figure 4A:
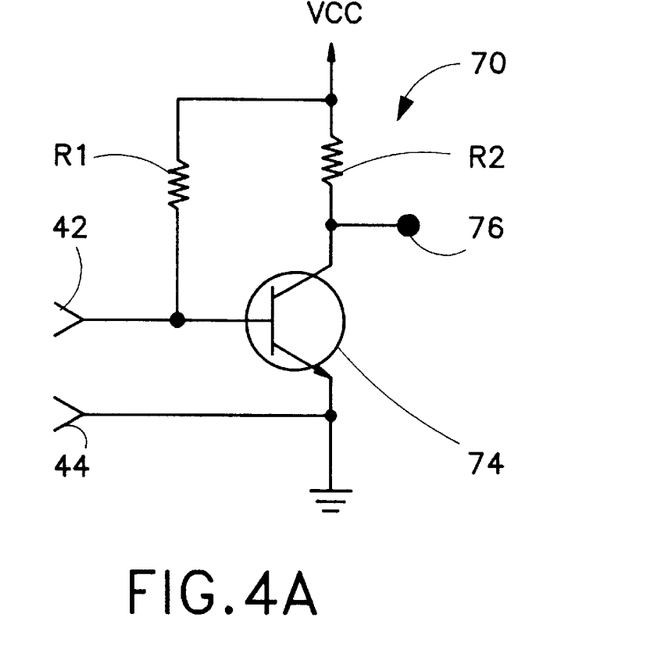
FIGS. 4A and 4B are circuit diagrams of two alternative medical instrument control or actuator circuits including contacts shown in FIGS. 2A and 3A.
Figure 4B:
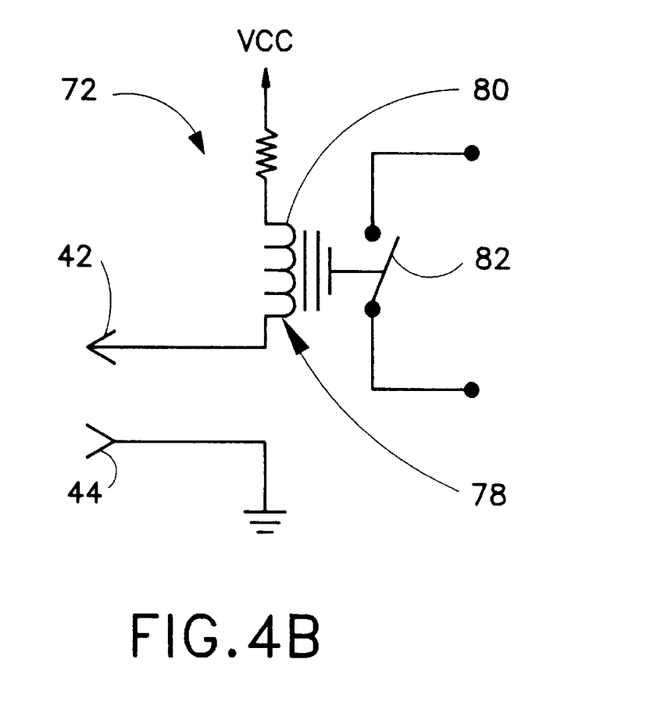

In operation, the surgeon will push on ring 24 with a thumb or finger. Ring 24 is slid forward (distally directed arrow 32) until conductive lining 38 contacts rivet heads 50 and 52. Since conductive lining 38 on ring 24 will effectively connect contact rivets 42 and 44 electrically, wire conductors 46 and 48 will be shorted together. This electrical connection may be sensed by electrical circuits well known to the art for purposes of initiating ultrasonic wave generation and emission, pump operation, or another action the user wishes to apply to organic tissues of a patient. Sample circuits 70 and 72 are shown in FIGS. 4A and 4B, respectively.

Circuit 70 includes an NPN transistor 74 having a base connected to one contact rivet 42 or 44 and an emitter connected to ground. A collector of transistor 74 is connected to a source of voltage Vcc via a resistor R2. The base of transistor 74 is also connected to source voltage Vcc, via another resistor R1. An output terminal 76 provides a control voltage.

Circuit 72 includes a relay 78 which conducts current upon a connecting of contact rivets 42 and 44 via lining or bridging contact 38. In that closed circuit, a coil 80 of relay 78 is grounded on one side via contacts 42, 44 and 38 and connected on an opposite side to source voltage Vcc via a resistor R3. Relay 78 operates a switch 82.

As illustrated in FIG. 2B, a connector 84 at a proximal end of handpiece case 26 has three contact pins 86, 88, and 90. One contact pin 88 is a ground contact, generally floating, while a second contact pin represents a power terminal for the piezoelectric crystal assembly 18, and the third contact pin 90 is a control contact operatively connected to a contact rivet 42 or 44 of the ring-actuated handpiece switch, the other rivet 44 or 42 being connected to pin 88.

When the surgeon releases manual pressure on ring 24, the energy contained in the compressed springs 56 and 58 will force the ring rearward, in proximal direction 34, until the ring contacts abutment 36. Conductive lining 38 then is disengaged from rivet heads 50 and 52, isolating them electrically once more. The electric circuit 70 or 72 will then sense this disengagement and the ultrasound or other action will cease.

Figure 5A:
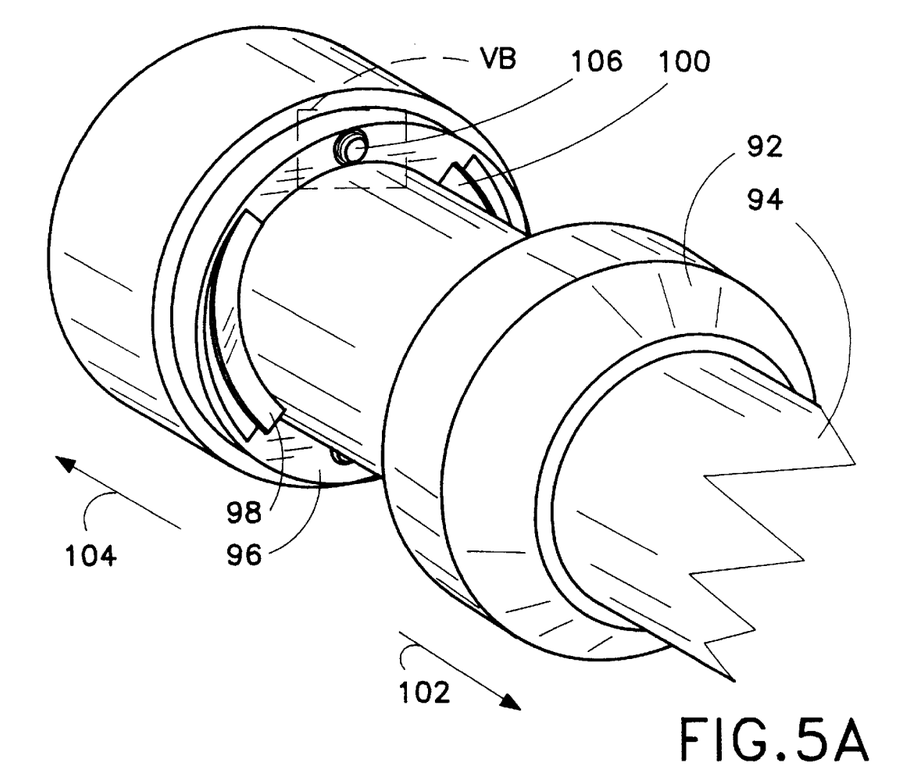
FIG. 5A is a partial isometric view of another medical instrument handpiece with a switch, in accordance with the present invention.

In FIG. 5A, an actuator ring 92 slidably mounted to a handpiece case 94 is spring loaded by a molded plastic leaf spring 96 glued or staked to handpiece face (not referenced). Arcuate leaf-spring fingers 98 and 100 project in a proximal direction 102 from the handpiece face and press against an annular conductive lining (not shown in FIG. 5A) similar to lining 38. When ring 92 is slid in a forward or distal direction 104, fingers 98 and 100 deform and allow the conductive ring lining to engage electrical contacts in the form of rivets 106, electrically shorting the rivets and initiating ultrasound activity. When ring 92 is released, fingers 98 and 100 push the ring in the proximal or rearward direction 102 until the ring contacts an abutment (not shown) on case 94. In this embodiment, ring 92 is free to rotate, which allows for self cleaning and reduces the need for high tolerance machining for pin holes. The self cleaning feature allows the contact surface of the lining or bridging contact to be kept free of debris or corrosion which may prevent effective electrical circuit closure. Another embodiment would be to press coil springs into a close tolerance hole located in the handpiece face. The springs would press against the ring conductive face and allow the ring to rotate freely. This embodiment requires short, stiff springs to be used, to prevent bending or twisting as the ring rotates.

Figure 5B:
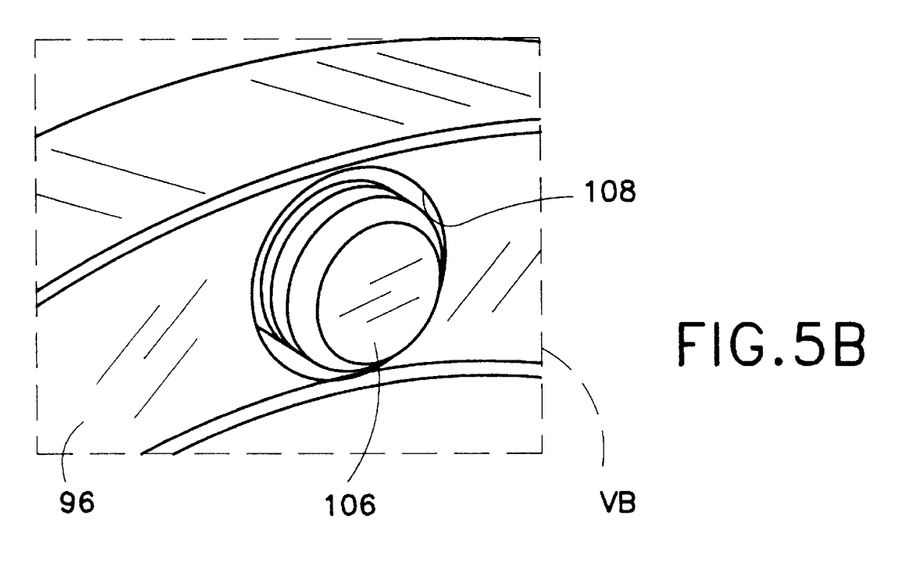
FIG. 5B is a partial isometric view of a detail VB of the handpiece of FIG. 5A.

Instead of being molded from thermoplastic, spring 96 of FIGS. 5A and 5B may be stamped from a noncorrosive metal. However, rivets 106 must be electrically isolated from this spring either by non conductive bushings or via clearance holes 108 in spring 96, as shown in FIG. 5B.

Figure 6A:
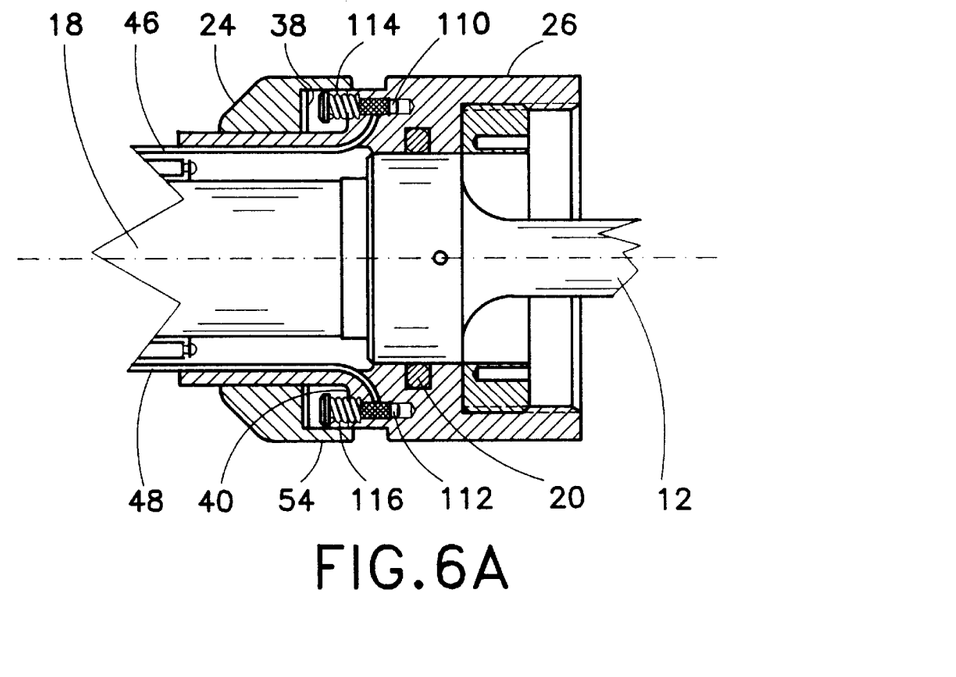
FIG. 6A is a partial longitudinal cross-sectional view of a modified medical instrument handpiece in accordance with the present invention, showing spring-loaded electrical contacts.
Figure 6B:
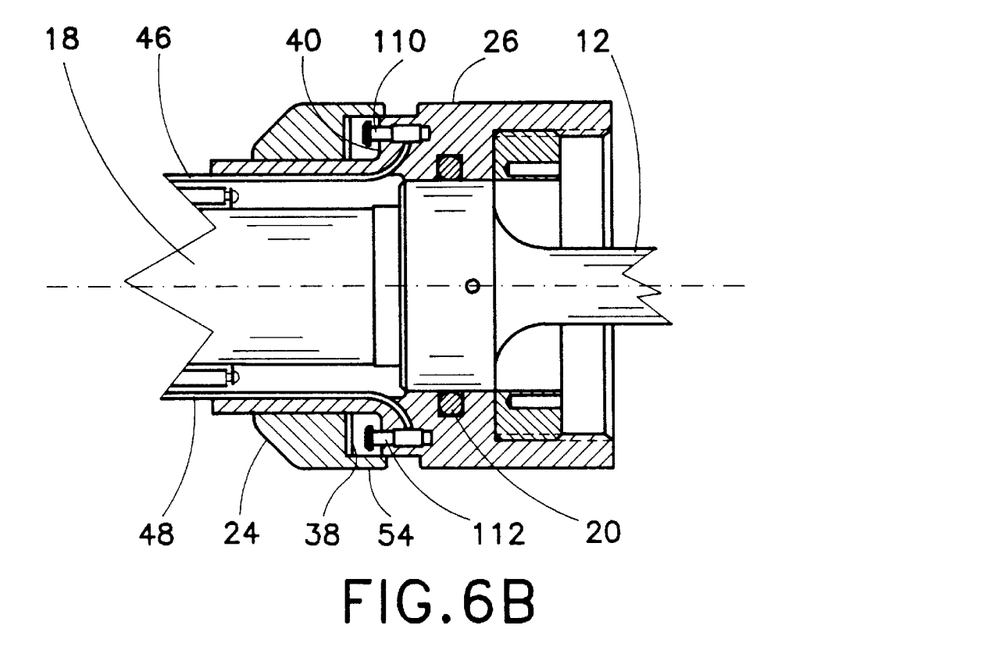
FIG. 6B is view of the modified medical instrument handpiece of FIG. 6A, simplified to illustrate an advantage of the modification.

In the embodiment shown in FIG. 3A, rivet heads 50 and 52 must extend from face 40 of handpiece case 26 by an equal amount. If the projected distance is substantially different, the conductive lining 38 of ring 24 may not make contact with both rivets 42 and 44 and therefore will not electrically short them. To prevent this, rivets 42 and 44 may be replaced with contact pins 110 and 112 which are loaded by respective surrounding helical springs 114 and 116 and accordingly have a self leveling feature, as shown in FIG. 6A. Thus, where one pin 110 projects further from face 40 of casing 26, as shown in FIG. 6B (omitting springs for simplicity), ring 24 will then depress that one pin 110 until the other pin 112 engages, providing positive engagement of both. Designers will note that many other self leveling devices are possible.

In order to assure that steam does not penetrate to the interior of handpiece 26 or 94, rivets 42, 44, 106 and/or pins 60, 62, 110, 112 may be molded in place or sealed with epoxy type sealants in standard manner. Since ring 24 or 94 does not require a wire to be attached to it, the number of case penetrations is minimized. All subcomponents are manufactured of readily available materials such as stainless steel or thermoplastics which have been approved for use in medical devices.

Figure 7:
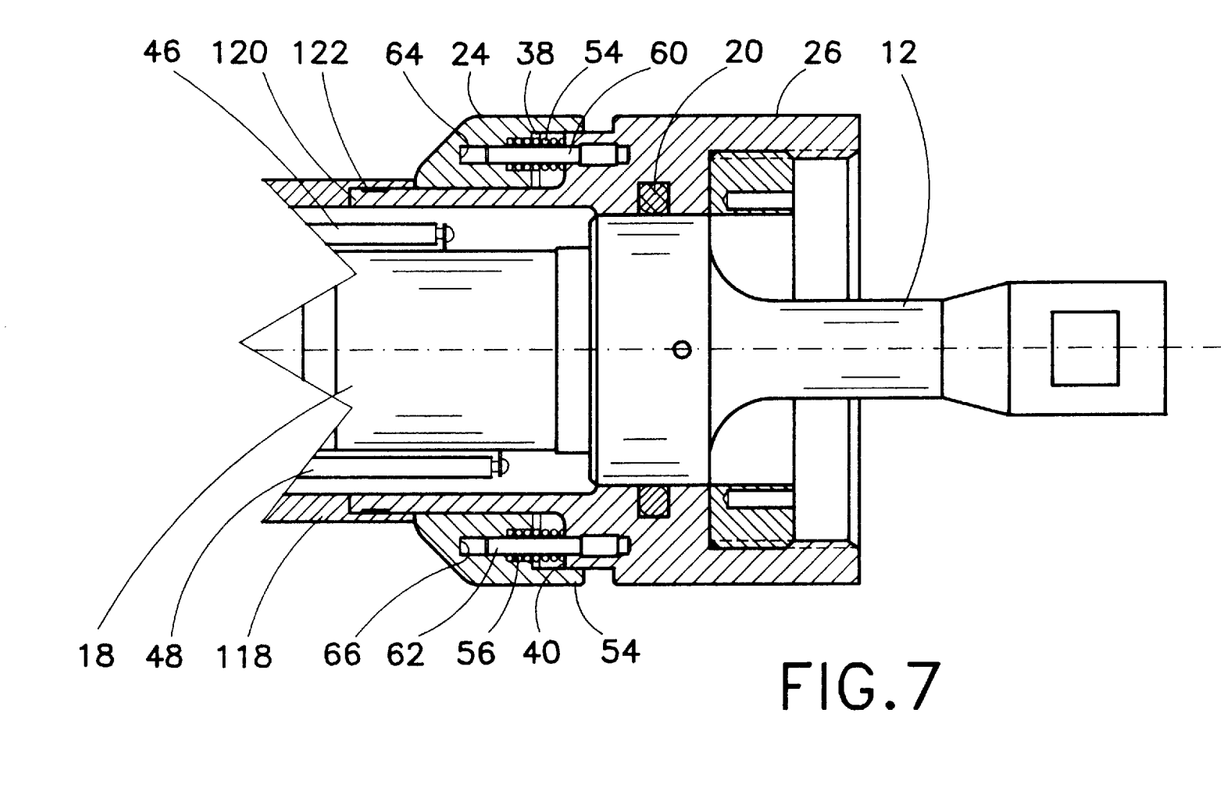
FIG. 7 is a partial longitudinal cross-sectional view of a medical instrument handpiece in accordance with the invention, illustrating a method of manufacture.
Figure 8A:
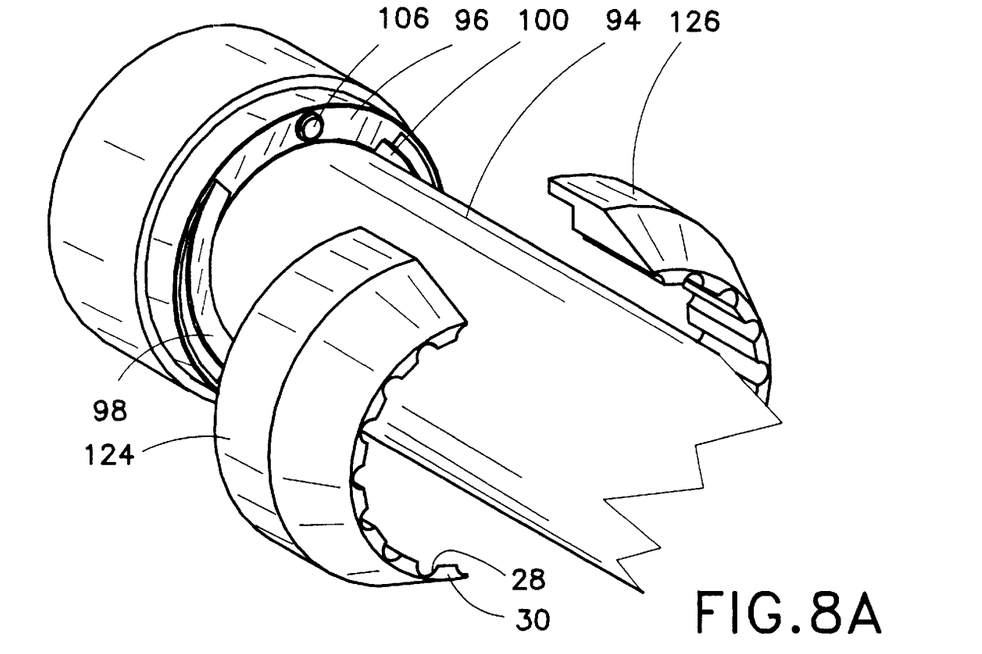
FIGS. 8A and 8B are partial isometric views of a medical instrument handpiece in accordance with the invention, illustrating two steps in another method of manufacture.
Figure 8B:
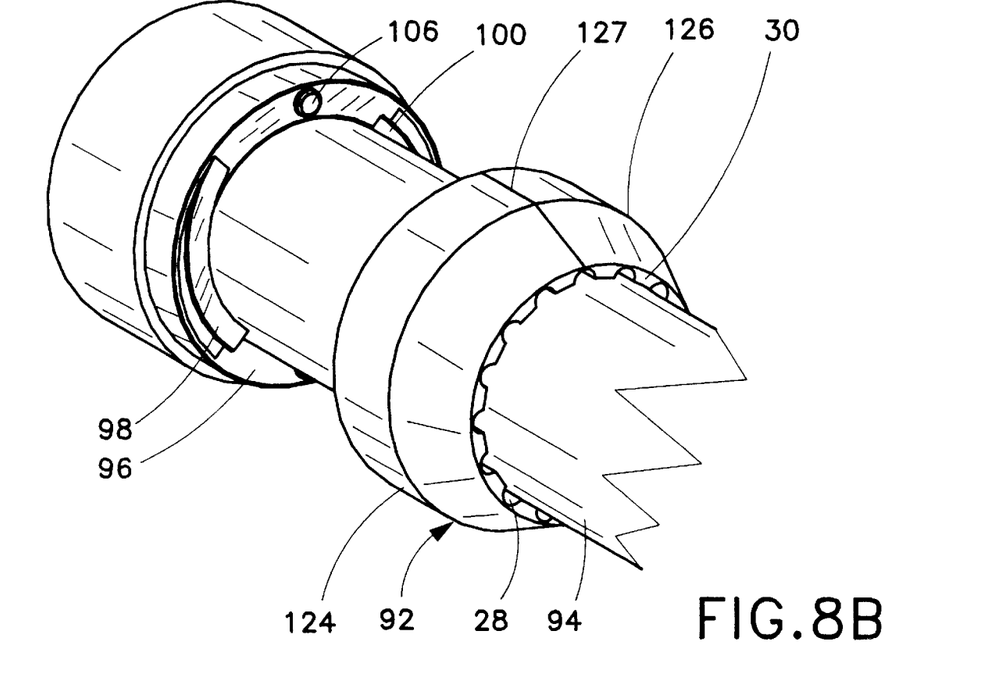

To facilitate assembly, handpiece case 26 (or 94) may be fashioned in two parts 118 and 120, as depicted in FIG. 7. Case 26 has adhesive 122 applied to the mating sufaces and then the assembly is pressed together. Alternatively, ring 92 (or 24) may be made in two semicircular sections 124 and 126 and glued together at 127, as shown in FIGS. 8A and 8B. Other methods may be employed, but those schooled in the art will realize that the method of manufacture does not alter the concept or scope of this disclosure.

Figure 9A:
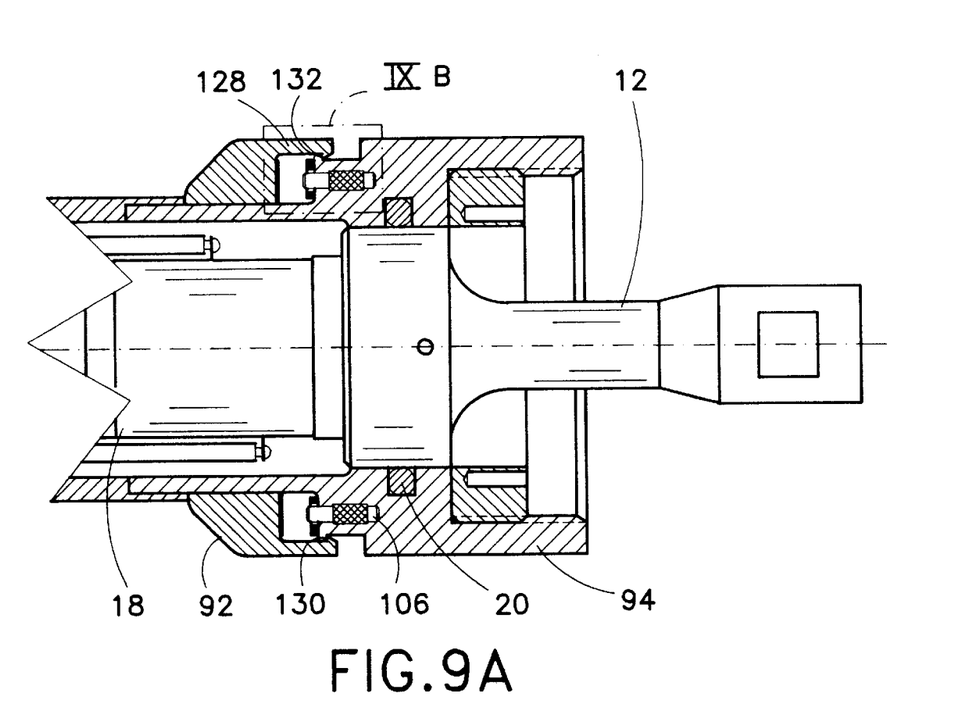
FIG. 9A is a partial longitudinal cross-sectional view of another modified medical instrument handpiece in accordance with the present invention.
Figure 9B:
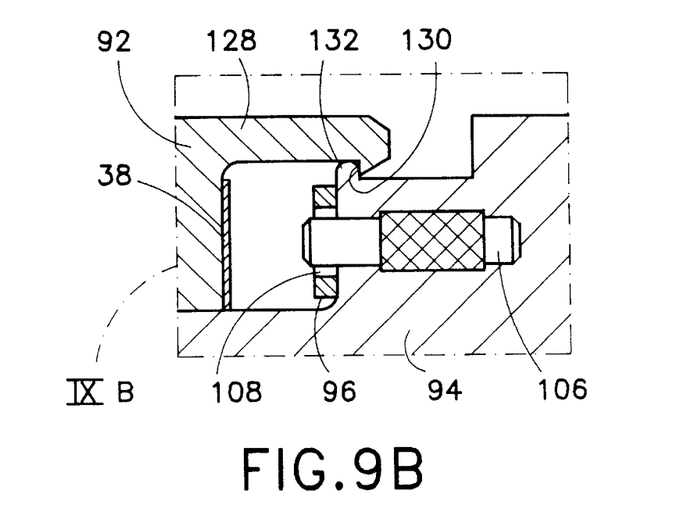
FIG. 9B is a partial longitudinal cross-sectional view of a detail IXB of the modified handpiece of FIG. 9A.

Although the embodiments described above are resistant to gumming or clogging by body fluids or other debris by virtue of grooves 28 and ribs 30 and the large clearances between members, provisions for cleaning under ring 24 or 92 may be desired to ensure sterility. To accomplish this, ring 92 (or 24) may be formed with an annular flange or cuff 128 having an inwardly projecting lip 130 at a free end, as shown in FIGS. 9A and 9B. This circumferential projection or lip 130 is located on an inner surface of cuff 128 and is generally assymmetrically triangular in cross section. A corresponding lip or shoulder 132 is formed on an outer diameter of handpiece case 94 (or 26) and may be rectangular, round or triangular in cross section. Cuff 128 may have longitudinally machined slots (not shown) which segment the cuff and render it more flexible, to thereby reduce engagement and disengagement forces. In this embodiment, handpiece case need not have abutment 36 to trap ring 24 in place. All other features of the embodiment are as disclosed above.

In assembling the embodiment of FIGS. 9A and 9B, ring 92 is pushed forward until lip 130 contacts shoulder 132 on handpiece case 94. Ring 92 is then pushed with greater force so that the segments expand over the case projection and then close back down around it. In this manner, ring 92 is held in place axially by the interlocking of lip 130 and shoulder 132 instead of by abutmnet 36 (FIG. 2A). After use, ring 92 is pulled back until the ring is clear of the projections. The ring may then be slid back, which exposes the interior surfaces which may then be cleaned. The area around the contacts on the handpiece face may similarly be cleaned. By making the cuff lip 130 asymmetrical, the force needed in removing ring 92 may be made greater than the force needed for assembly, which insures cuff 128 will not disengage during use.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A handpiece assembly for a medical instrument, comprising:

a handle having an axis extending from a proximal end of the instrument toward a distal end thereof;

an electrical circuit incorporated at least partially in said handle for controlling an application of an action to a patient via the medical instrument, said circuit having a first electrical contact and a second electrical contact each projecting from a surface of said handle, said first electrical contact and said second electrical contact being disposed in a plane oriented transversely to said axis, said surface being an annular surface extending in said plane transversely to said axis and facing toward said proximal end of said handle, said first electrical contact and said second electrical contact projecting from said annular surface toward said proximal end of said handle, said first electrical contact and said second electrical contact being angularly spaced from one another about said axis;

an actuator ring slidably disposed on said handle and surrounding same for motion in alternately opposite directions along said handle under the control of an operator; and a bridging electrical contact disposed on said ring for conductively connecting said first electrical contact and said second electrical contact at a first predetermined longitudinal position of said ring along said handle, thereby closing said circuit at said first predetermined longitudinal position of said ring, and for opening said circuit at another longitudinal position of said ring along said handle.

2. The assembly defined in claim 1, further comprising a spring disposed between said handle and said ring for biasing said ring in one direction along said handle and thereby biasing bridging contact out of engagement with said first electrical contact and said second electrical contact.

3. The assembly defined in claim 2 wherein said spring is a helical spring.

4. The assembly defined in claim 3 wherein said spring is disposed about a pin extending from said annular surface in a proximal direction into a recess in said ring, said pin being different from said first electrical contact and said second electrical contact.

5. The assembly defined in claim 3 wherein said spring is one of two helical springs disposed between said handle and said ring for biasing said bridging contact out of engagement with said first electrical contact and said second electrical contact, said springs being disposed on opposite sides of said handle, said first electrical contact and said second electrical contact being disposed at positions displaced 90° from said springs.

6. The assembly defined in claim 2 wherein said spring is a leaf spring attached to said annular surface.

7. The assembly defined in claim 1 wherein said ring is provided with an annular flange or cuff surrounding said annular surface.

8. The assembly defined in claim 7 wherein said flange or cuff is provided along a free edge with an inwardly extending lip, said handle being provided with an outwardly projecting shoulder formation cooperating with said lip to limit axial motion of said ring in a proximal direction.

9. The assembly defined in claim 1 wherein said ring is provided along a radially inner side with a plurality of grooves extending parallel to said axis to define a series of ribs engaging said handle.

10. The assembly defined in claim 1 wherein said first electrical contact and said second electrical contact are spring biased.

11. The assembly defined in claim 1 wherein said bridging electrical contact is annular.

12. The assembly defined in claim 1, further comprising an arrest on said handle for limiting axial motion of said ring in a proximal direction.

13. A handpiece for a medical instrument, comprising:
a handle having an axis extending from a proximal end of the instrument toward a distal end thereof;
an electrical circuit incorporated at least partially in said handle for controlling an application of an action to a patient via the medical instrument, said circuit having a first electrical contact and a second electrical contact each projecting from a surface of said handle, said first electrical contact and said second electrical contact being spaced from one another;
an actuator ring slidably disposed on said handle and surrounding same for motion in alternately opposite directions along said handle under the control of an operator;
a bridging electrical contact disposed on said ring for conductively connecting said first electrical contact and said second electrical contact at a first predetermined longitudinal position of said ring along said handle, thereby closing said circuit at said first predetermined longitudinal position of said ring, and for opening said circuit at another longitudinal position of said ring along said handle; and
a spring disposed between said handle and said ring for biasing said ring towards one end of said handle, thereby serving to shift said bridging contact out of engagement with said first electrical contact and said second electrical contact.

14. The assembly defined in claim 13 wherein said surface is disposed in a transverse plane relative to said axis, said spring being a helical spring having a spring axis oriented substantially parallel to the axis of said handle.

15. The assembly defined in claim 14 wherein said spring is disposed about a pin extending from said surface along said spring axis into a recess in said ring, said pin being different from said first electrical contact and said second electrical contact.

16. The assembly defined in claim 14 wherein said spring is one of two helical springs disposed between said handle and said ring for biasing said ring towards said one end of said handle, said springs being disposed on opposite sides of said handle, said first electrical contact and said second electrical contact being disposed at positions displaced 90° from said springs.

17. The assembly defined in claim 13 wherein said spring is a leaf spring attached to said surface.

18. The assembly defined in claim 17 wherein said surface is an annular surface disposed in a transverse plane relative to said axis, said leaf spring extending in an arc about said axis and along said surface.

19. A handpiece for a medical instrument, comprising:
a handle having an axis extending from a proximal end of the instrument toward a distal end thereof;
an electrical circuit incorporated at least partially in said handle for controlling an application of an action to a patient via the medical instrument, said circuit having a first electrical contact and a second electrical contact each projecting from a surface of said handle, said first electrical contact and said second electrical contact being spaced from one another;
an actuator ring slidably disposed on said handle and surrounding same for motion in alternately opposite directions along said handle under the control of an operator; and
a bridging electrical contact disposed on said ring for conductively connecting said first electrical contact and said second electrical contact at a first predetermined longitudinal position of said ring along said handle, thereby closing said circuit at said first predetermined longitudinal position of said ring, and for opening said circuit at another longitudinal position of said ring along said handle,
said ring being provided with an annular flange or cuff extending over said handle and surrounding said first electrical contact, said second electrical contact and said bridging electrical contact to define an annular chamber in which said first electrical contact, said second electrical contact and said bridging electrical contact are located.

20. The assembly defined in claim 19 wherein said annular flange or cuff is provided along a free edge with an inwardly extending lip, said handle being provided with an outwardly projecting shoulder formation cooperating with said lip to limit axial motion of said ring in one direction parallel to said axis.

21. The assembly defined in claim 20 wherein said annular flange or cuff is resilient to attach said ring to said handle in a snap-lock fit of said lip over said shoulder.

22. A handpiece for a medical instrument, comprising:

a handle having an axis extending from a proximal end of the instrument toward a distal end thereof;

an electrical circuit incorporated at least partially in said handle for controlling an application of an action to a patient via the medical instrument, said circuit having a first electrical contact and a second electrical contact each projecting from a surface of said handle, said first electrical contact and said second electrical contact being spaced from one another;

an actuator ring slidably disposed on said handle and surrounding same for motion in alternately opposite directions along said handle under the control of an operator; and a bridging electrical contact disposed on said ring for conductively connecting said first electrical contact and said second electrical contact at a first predetermined longitudinal position of said ring along said handle, thereby closing said circuit at said first predetermined longitudinal position of said ring, and for opening said circuit at another longitudinal position of said ring along said handle, said ring being provided along a radially inner side with a plurality of grooves extending parallel to said axis to define a series of ribs engaging said handle.

23. A handpiece for a medical instrument, comprising:

a handle having an axis extending from a proximal end of the instrument toward a distal end thereof;

an electrical circuit incorporated at least partially in said handle for controlling an application of an action to a patient via the medical instrument, said circuit having a first electrical contact and a second electrical contact each projecting from a surface of said handle, said first electrical contact and said second electrical contact being spaced from one another, said first electrical contact and said second electrical contact being spring biased;

an actuator ring slidably disposed on said handle and surrounding same for motion in alternately opposite directions along said handle under the control of an operator; and a bridging electrical contact disposed on said ring for conductively connecting said first electrical contact and said second electrical contact at a first predetermined longitudinal position of said ring along said handle, thereby closing said circuit at said first predetermined longitudinal position of said ring, and for opening said circuit at another longitudinal position of said ring along said handle.

\* \* \* \* \*